US010413749B2

(12) United States Patent
Kruecker et al.

(10) Patent No.: US 10,413,749 B2
(45) Date of Patent: Sep. 17, 2019

(54) DUAL LOCALIZATION OF BRACHYTHERAPY RADIOACTIVE SEEDS

(71) Applicant: KONINKLIJKE PHILIPS N.V., Eindhoven (NL)

(72) Inventors: Jochen Kruecker, Washington, DC (US); Ehsan Dehghan Marvast, New York, NY (US); Shyam Bharat, Arlington, MA (US); Cynthia Ming-Fu Kung, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/513,608

(22) PCT Filed: Sep. 25, 2015

(86) PCT No.: PCT/IB2015/057390

§ 371 (c)(1),
(2) Date: Mar. 23, 2017

(87) PCT Pub. No.: WO2016/046801

PCT Pub. Date: Mar. 31, 2016

(65) Prior Publication Data

US 2018/0229053 A1 Aug. 16, 2018

Related U.S. Application Data

(60) Provisional application No. 62/055,902, filed on Sep. 26, 2014.

(51) Int. Cl.
*A61N 5/10* (2006.01)
*A61B 6/03* (2006.01)
(Continued)

(52) U.S. Cl.
CPC ........... *A61N 5/1007* (2013.01); *A61B 6/032* (2013.01); *A61B 8/0841* (2013.01); *A61B 34/20* (2016.02);
(Continued)

(58) Field of Classification Search
CPC .. A61N 5/1007; A61N 5/1027; A61N 5/1071; A61N 5/1039; A61N 2005/1024;
(Continued)

(56) References Cited

U.S. PATENT DOCUMENTS 6,471,710 B1 * 10/2002 Bucholtz .............. G01B 11/005 600/229
6,610,013 B1 * 8/2003 Fenster .................. A61N 5/103 600/439
(Continued)

*Primary Examiner* — Navin Natnithithadha
*Assistant Examiner* — Sunita Reddy

(57) ABSTRACT

A brachytherapy seed localization system for localizing radioactive seeds within a diseased tissue, the brachytherapy seed localization system employs a tool tracking machine (50) for generating a tracked seed distribution map (51) of delivered locations of the radioactive seeds within the diseased tissue, and a tissue imaging machine (60) for generating a seed distribution image (61) of projected locations of the radioactive seeds within the diseased tissue including at least one false projected location. The brachytherapy seed localization system further employs a brachytherapy seed localizer (70) for generating a composite seed distribution map (71) of estimated locations of the radioactive seeds within the diseased tissue derived from a combination of the tracked seed distribution map (51) and the seed distribution image (61) excluding any false projected location(s) within the seed distribution image (61).

15 Claims, 14 Drawing Sheets

(51) Int. Cl.

| | |
|---|---|
| ***A61B 8/08*** | (2006.01) |
| ***A61B 34/20*** | (2016.01) |
| *A61B 5/055* | (2006.01) |

(52) U.S. Cl.
CPC ......... *A61N 5/1027* (2013.01); *A61N 5/1039* (2013.01); *A61N 5/1071* (2013.01); *A61B 5/055* (2013.01); *A61B 2034/2051* (2016.02); *A61B 2034/2063* (2016.02); *A61N 5/1048* (2013.01); *A61N 2005/1024* (2013.01)

(58) Field of Classification Search
CPC ....... A61B 6/032; A61B 8/0841; A61B 34/20; A61B 5/055; A61B 2034/2051; A61B 2034/2063
USPC .......................................................... 600/1–8
See application file for complete search history.

(56) References Cited

U.S. PATENT DOCUMENTS

2003/0065260 A1* 4/2003 Cheng .................. A61B 8/0833 600/427
2004/0092786 A1 5/2004 Zaider et al.
2008/0095422 A1* 4/2008 Suri ..................... G06K 9/6206 382/131
2008/0188705 A1* 8/2008 Lubock ................ A61N 5/1015 600/8
2008/0281143 A1* 11/2008 Lubock ................ A61N 5/1015 600/3
2009/0014015 A1 1/2009 Tutar et al.
2009/0030259 A1* 1/2009 Quick .................. A61N 5/1015 600/4
2009/0136108 A1* 5/2009 Badiei ....................... G06T 7/12 382/131
2009/0198094 A1* 8/2009 Fenster ................ A61B 8/0833 600/3
2009/0209805 A1* 8/2009 Lubock ................ A61N 5/1015 600/7
2010/0204534 A1* 8/2010 Damarati .......... A61M 25/0029 600/3
2010/0312038 A1* 12/2010 Shechter .............. A61N 5/1015 600/3
2013/0102891 A1* 4/2013 Binnekamp .......... A61N 5/1007 600/424
2015/0306426 A1 10/2015 Marvast et al.

* cited by examiner

Stage S92 (reconstructed seed distribution map)

Stage S96 (composite seed distribution image)

DUAL LOCALIZATION OF BRACHYTHERAPY RADIOACTIVE SEEDS

CROSS-REFERENCE TO PRIOR APPLICATIONS

This application is the U.S. National Phase application under 35 U.S.C. § 371 of International Application Serial No. PCT/IB2015/057390, filed on Sep. 25, 2015, which claims the benefit of U.S. Application Ser. No. 62/055,902, filed on Sep. 26, 2014. These applications are hereby incorporated by reference herein.

The present invention generally relates to brachytherapy procedures for the insertion of radioactive seeds within diseased tissue (e.g., low dose rate ("LDR") brachytherapy for prostate cancer). The present invention specifically relates to a localization of the radioactive seeds within the diseased tissue derived from a combination of an accuracy of tissue imaging of the radioactive seeds as projected within the diseased tissue (e.g., ultrasound seed localization) with a robustness of a tool tracking of a delivery of the radioactive seeds by applicators (e.g., needles) to planned locations within the diseased tissue (e.g., electromagnetic seed localization).

In LDR brachytherapy, radioactive seeds are delivered within the diseased tissue to provide radioactive therapy locally into the diseased tissue. For example, FIG. 1 illustrates a brachytherapy delivery system employing a brachytherapy planner 30, a tool tracking machine 50 (e.g., an electromagnetic ("EM") tracking machine, an optical tracking machine, and a shape sensing tracking machine), and a tissue imaging machine 60 (e.g., an ultrasound imaging machine and X-ray machine.

Generally, in operation, brachytherapy planner 30 generates a planned seed distribution map 31 for delivering radioactive seeds within a diseased tissue 20. More particularly in order to achieve a clinically prescribed overall radioactive dose distribution within the diseased tissue, planned seed distribution map 31 includes locations of a specific number of radioactive seeds within a pre-operative image of the diseased tissue 20 (e.g., ultrasound imaging or magnetic resonance imaging or a computed-tomography scan) whereby a brachytherapy therapist attempts to deliver the radioactive seeds via applicators (e.g., needles) to the planned locations within diseased tissue 20 under guidance by tool tracking machine 50 and tissue imaging machine 60).

During the LDR brachytherapy, precise delivery of the radioactive seeds into diseased tissue 20 in accordance with the brachytherapy plan is difficult for several reasons, most importantly being any deformation of the diseased tissue subsequent to the pre-operative imaging of the diseased tissue due to (1) any external force(s) acting upon the diseased tissue and (2) any internal force(s) within the diseased tissue generated from (a) a biological functioning of the diseased tissue and/or (b) movement of the delivery applicator(s) within the diseased tissue. Consequently, resting locations of radioactive seeds within the diseased tissue may be translationally and/or rotationally divergent from the planned locations of the radioactive seeds within the diseased tissue. For example, FIG. 2A illustrates a planar view 31P of a planned seed distribution map 31 (FIG. 1) showing planned locations for radioactive seeds RS1-RS25 within diseased tissue 20 via delivery by applicator needles 41*a*-41*e*, and FIG. 1B illustrates a planar view 20P of possible horizontal and vertical forces acting upon the planned locations of radioactive seeds RS1-RS25 within the diseased tissue 20 as symbolized by the arrows.

Referring back to FIG. 1, tracking seed localization as known in the art involves a tracking of applicators for the delivery of the radioactive seeds to the planned locations relative to a reference coordinate system 42 registered with diseased tissue 20. However, since the tracking of the applicators may be inherently imprecise to a slight degree and since diseased tissue 20 may deform as previously stated herein, the radioactive seeds may be dropped to delivery locations and/or may move to resting locations divergent from the planned locations of the radioactive seeds. Consequently, any estimation of a radioactive dose distribution within diseased tissue 20 as a function of the tracking seed localization may be inaccurate.

More particularly, tool tracking machine 50 generates a tracked seed distribution map 51 of delivery locations of the radioactive seeds within diseased tissue 20 as the radioactive seeds are being delivered to diseased tissue 20 in accordance with planned seed distribution map 31. Ideally, maps 31 and 51 are identical. However, as previously stated, the radioactive seeds may be dropped to delivery locations of map 51 and/or may move to resting locations divergent from the planned locations of map 31.

For example, FIG. 3A illustrates an ideal planar view 51P of tracked seed distribution map 51 showing delivery locations for radioactive seeds RS1-RS25 within diseased tissue 20 in accordance with planned seed distribution map 31, and FIG. 3B illustrates a typical planar view 51T of tracked seed distribution map 51 showing actual delivery locations of radioactive seeds RS1-RS25 within diseased tissue 20. A divergence of planar views 51P and 5 of tracked seed distribution map 51 is primarily due to any deformation of diseased tissue 20 subsequent to the pre-operative imaging of diseased tissue 20, particularly subsequent to delivery of radioactive seeds RS1-RS25, as symbolized by the black background of radioactive seeds RS1-RS25 as shown in FIG. 3B. Thus, while robust in terms of a complete tracking of all delivered locations within diseased tissue, an accuracy of the tracking seed localization in delivering and resting the radioactive seeds to the planned locations is limited.

Referring again to FIG. 1, imaging seed localization as known in the art involves tissue imaging machine 60 generating a seed distribution image 61 of projected locations of the radioactive seeds within diseased tissue 20 after seed delivery in accordance with planned seed distribution map 31 to account for any motion of the radioactive seed(s) primarily due to any deformation of diseased tissue 20. Imaging seed localization tends to achieve a better overall accuracy than the accuracy of tracking seed localization as previously described herein, particularly for radioactive seeds with considerable post-delivery motion. However, an accuracy of the imaging seed localization may be limited by false projected locations due to a poor visibility level of one or more radioactive seeds within seed distribution image 61 and/or any image artifacts within seed distribution image 61. More particularly, (1) a false negative projected location within seed distribution image 61 is derived from a poor visibility level of a radioactive seed, (2) a false positive projected location within seed distribution image 61 is derived from an image artifact, and (3) any false negative and/or false positive projected location(s) limit the accuracy by seed distribution image 61 of resting locations of the radioactive seeds within diseased tissue 20. Consequently, any estimation of a radioactive dose distribution within diseased tissue 20 as a function of the imaging seed localization may be inaccurate.

For example, FIG. 4A illustrates an ideal planar view 61I of seed tissue image 61 showing projected locations of radioactive seeds RS1-RS25 as shown in FIG. 3B void of any false negative and any false positive projected locations, and FIG. 4B illustrates a typical planar view 61T of seed tissue image 61 showing projected locations of radioactive seeds RS1-RS25 as shown in FIG. 3B inclusive of false negative projected locations FN1-FN4 and false positive projected locations FP1-FP5. False negative projected locations FN1-FN4 are derived from poor visibility levels of radioactive seeds RS2, RS10, RS13 and RS22 within typical planar view 61T of seed tissue image 61 as opposed to ideal planar view 61I of seed tissue image 61, and false positive projected locations FP1-FP5 are derived from image artifacts within typical planar view 61T of seed tissue image 61 that are not present in ideal planar view 61I of seed tissue image 61. While an accuracy of projected locations for radioactive seeds RS1-RS25 within tissue image 61 as shown in FIG. 4A is achievable, inherent tissue imaging limitations tend to, but not always, result in false negative and/or false positive projected location(s) within tissue image 61 as exemplary shown in FIG. 4B.

The present invention recognizes an importance for intra-procedural feedback as to whether or not a desired dose distribution of radioactive seeds within diseased tissue 20 is achieved in accordance with a brachytherapy plan to better impede any under-treatment and/or over-treatment of diseased tissue and to better impede any inadvertent treatment of bordering healthy tissue. To provide such intra-procedural feedback, the present invention uniquely combines an accuracy achievable by ultrasound seed localization with a robustness of electromagnetic tracking localization that overcomes potential individual disadvantages of ultrasound seed localization and electromagnetic seed localization.

One form of the present invention is brachytherapy seed localization system for localizing radioactive seeds within a diseased tissue. To this end, the brachytherapy seed localization system employs a tool tracking machine, a tissue imaging machine and a brachytherapy seed localizer.

In operation, the tool tracking machine generates a tracked seed distribution map of delivery locations of the radioactive seeds within the diseased tissue. For purposes of the present invention, the phrase 'tracked seed distribution map of delivery locations" broadly encompasses a map of each recorded location of a radioactive seed drop in the diseased tissue via a tracked applicator in accordance with a planned seed distribution map. A delivery location of a radioactive seed may be divergent from the planned location of the radioactive seed as well as the resting location of the radioactive seed, particularly for radioactive seeds that move after delivery into the diseased tissue.

The tool imaging machine generates a seed distribution image of projected locations of the radioactive seeds within the diseased tissue that may include one or more false projected locations. For purposes of the present invention, the phrase 'seed distribution image of projected locations" broadly encompasses an image of tissue image projections of resting locations of the radioactive seeds in the diseased tissue. Any false projected location(s) included within the tissue image projections include one or more false negative projected locations derived from a poor visibility level of radioactive seed(s) and/or one or more false positive projected locations derived from image artifact(s).

Responsive to the generation of the tracked seed distribution map and the seed distribution image, the brachytherapy seed localizer generates a composite seed distribution map of estimated locations of the radioactive seeds within the diseased tissue derived from a combination of the tracked seed distribution map and the seed distribution image excluding any false projected location(s) within the seed distribution image. For purposes of the present invention, the phrase 'composite seed distribution map of estimated locations" broadly encompasses a map of one or more delivery locations of the tracked seed distribution map and/or one or more projected locations of the seed distribution image.

Furthermore, the combination of the tracked seed distribution map and the seed distribution image may broadly encompass an application of a distance metric between the tracked seed distribution map and the seed distribution image for (1) confirming one or more of the projected locations, (2) recovering any identified false negative projected location(s) into the seed distribution image, and/or (3) removing any identified false positive projected location(s) from the seed distribution image. More particularly, the brachytherapy seed localizer may generate a reconstructed seed distribution map of extracted projected locations from the seed distribution image and apply a distance metric between assignable pairs of radioactive seeds between reconstructed seed distribution map and the tracked seed distribution map to generate the composite seed distribution map.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 5:
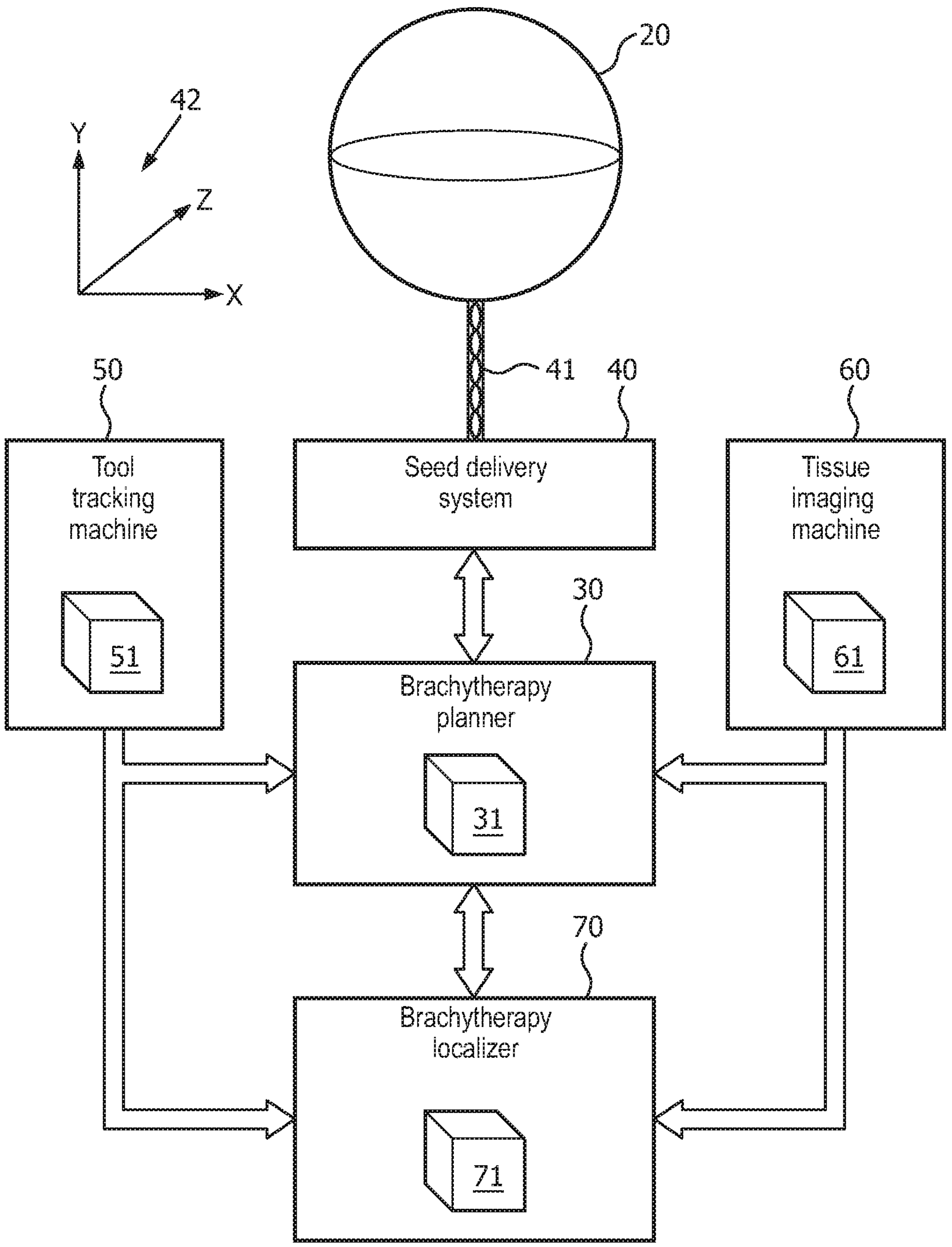
FIG. 5 illustrates an exemplary embodiment of a brachytherapy localization system in accordance with the present invention.

To facilitate an understanding of the present invention, exemplary embodiments of the present invention will be provided herein directed to a description of a brachytherapy localizer 70 of the present invention as shown in FIG. 5 for providing intra-procedural feedback of radioactive seed localization within diseased tissue 20 (e.g., a cancerous prostate). Furthermore, while tool tracking machine 50 and tissue imaging machine 60 are respectively embodied as an electromagnetic tracking machine 50 and an ultrasound imaging machine 60 in the description of FIGS. 5-16, in practice tool tracking machine 50 and tissue imaging machine 60 may be embodied in any form suitable for implementing the present invention.

Referring to FIG. 5, a brachytherapy localization system employs a seed delivery system 40, a brachytherapy planner 30, an electromagnetic tracking machine 50, an ultrasound imaging machine 60 and brachytherapy localizer 70.

Seed delivery system 40 is structurally configured as known in the art for delivering radioactive seeds to diseased tissue 20 via applicator needles 41.

Brachytherapy planner 30 is structurally configured as known in the art for planning the implantation of needles 41 into diseased tissue 20 and for planning a distribution of radioactive seeds within diseased tissue 20 to achieve a desired dose distribution within diseased tissue 20.

Electromagnetic tracking machine 50 is structurally configured as known in the art for electromagnetically tracking applicator needles 41 and an imaging probe of the ultrasound imaging machine 60 relative to a 3D reference coordinate system 42. The result is a generation of a 3D tracked seed distribution map 51 of delivery locations of radioactive seeds within diseased tissue 20.

Ultrasound imaging machine 60 is structurally configured as known in the art for ultrasound imaging diseased tissue 20 relative to 3D reference coordinate system 42. The result is a generation of a 3D seed distribution image 61 of projected locations of radioactive seeds within diseased tissue 20.

Brachytherapy localizer 70 is structurally configured in accordance with present invention for computing a composite seed distribution map 71 of estimated locations of the radioactive seeds within diseased tissue 20 derived from a combination of the electromagnetic seed localization by electromagnetic tracking machine 50 and the ultrasound seed localization by ultrasound image machine 60. In practice, brachytherapy localizer 70 may be (1) a stand-alone workstation, (2) a module installed within brachytherapy planner 30, electromagnetic tracking machine 50 and/or ultrasound machine 60, or (3) a modular network distributed across brachytherapy planner 30, electromagnetic tracking machine 50 and/or ultrasound machine 60. Also in practice, brachytherapy localizer 70 may input tracking data from electromagnetic tracking machine 50 for generating tracked seed distribution map 51 and/or imaging data from ultrasound imaging machine for generating seed distribution image 61.

In general operation, brachytherapy planner 30 is operated to plan an implantation of applicator needles 41 and radioactive seeds into diseased tissue 20 relative to a preoperative imaging of diseased tissue 20.

Upon generation and any refinement of the planned seed distribution map and any necessary reinsertion of application needles 41, seed delivery system 40 is operated to deliver the radioactive seeds within diseased tissue 20 in accordance with the planned seed distribution map, and electromagnetic tracking machine 50 is operated to electromagnetically track a delivery of the radioactive seeds within diseased tissue 20 to thereby generate tracked seed distribution map 51 of delivery locations of all radioactive seeds within diseased tissue 20. As previously stated herein, the delivery location(s) typically will be divergent from the planned location(s) of radioactive seeds within diseased tissue 20.

After delivery of radioactive seeds preferably on an applicator-by-applicator basis, ultrasound machine 60 is operated to generate ultrasound image of the resting locations of radioactive seeds within diseased tissue 20 to thereby generate seed distribution image 61 of projected locations of radioactive seeds within diseased tissue 20. As previously stated herein, the projected locations will typically be divergent from the resting locations, and the projected locations may be inclusive of false negative projected location(s) and/or false positive projected location(s). As such, preferably on an applicator-by-applicator basis after a deployment of a minimum number of applicators (e.g., five (5) applicators), brachytherapy localizer 70 combines tracking seed distribution map 51 and seed distribution image 61 to thereby compute composite seed distribution map 71 of estimated locations of the radioactive seeds within diseased tissue 20. The estimated locations include one or more delivery locations of the tracked seed distribution map and/or one or more projected locations of the seed distribution image exclusive of any false projected location(s) within seed distribution image 61 as exemplary shown in FIG. 6.

Figure 3A:
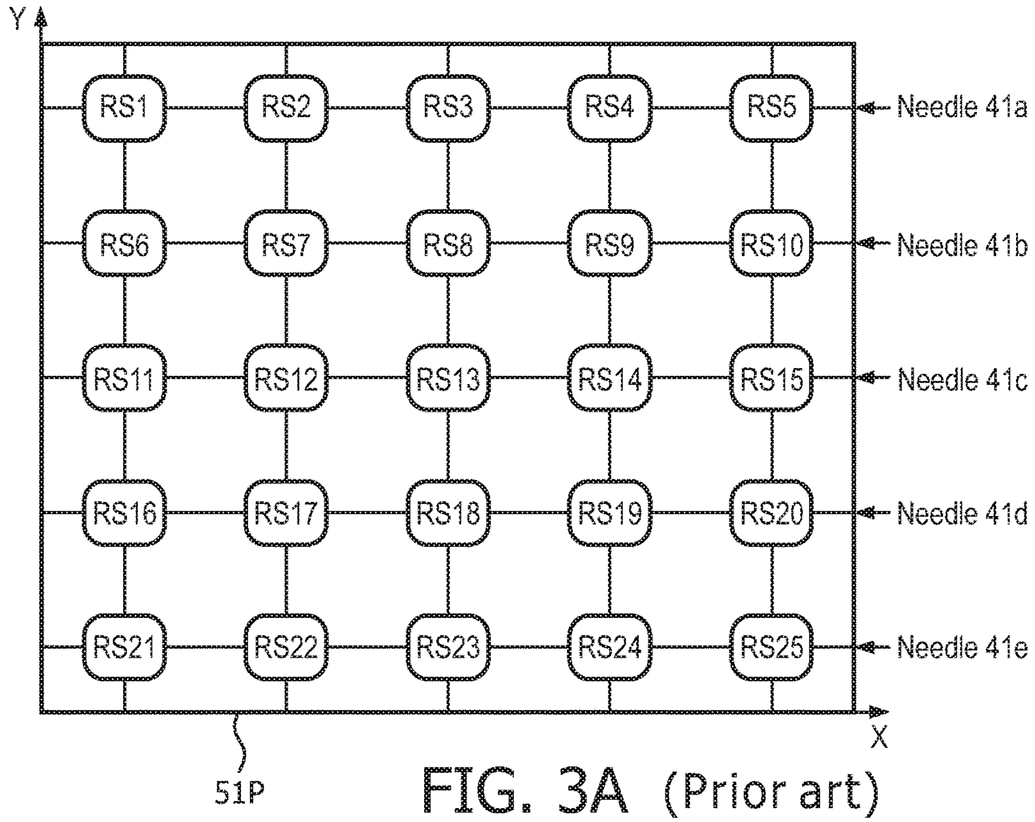
FIGS. 3A and 3B illustrate exemplary 2D views of brachytherapy tracked seed distribution maps as known in the art.
Figure 3B:
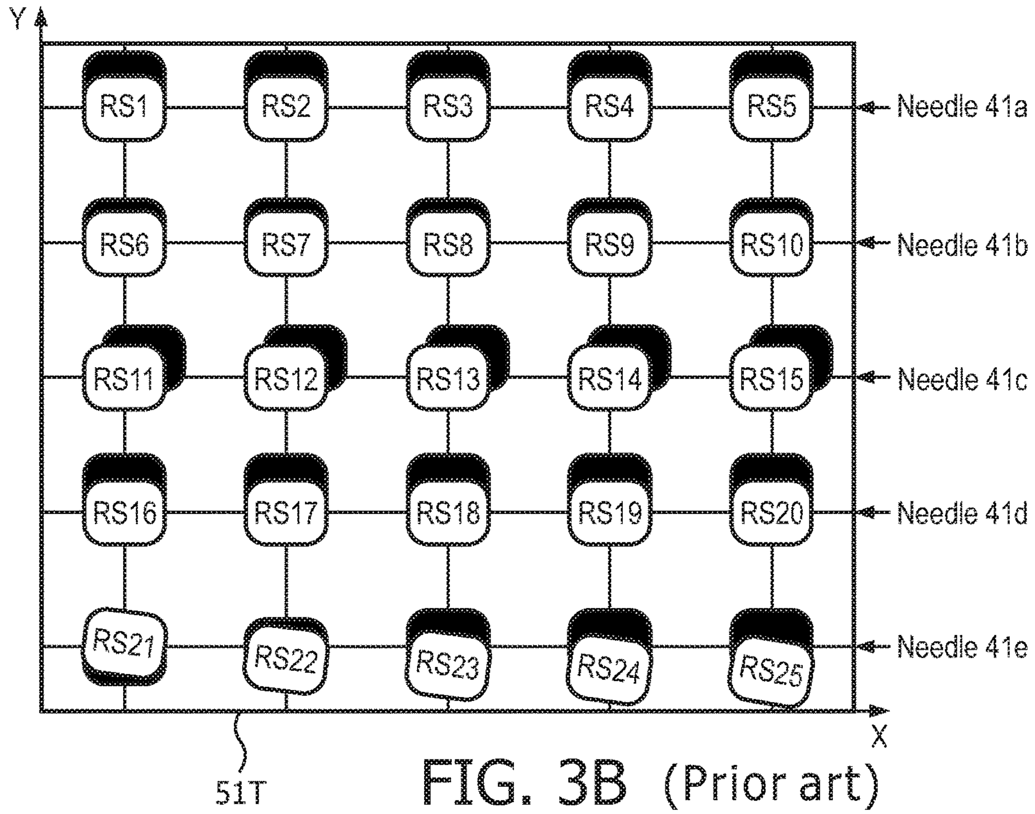
Figure 4A:
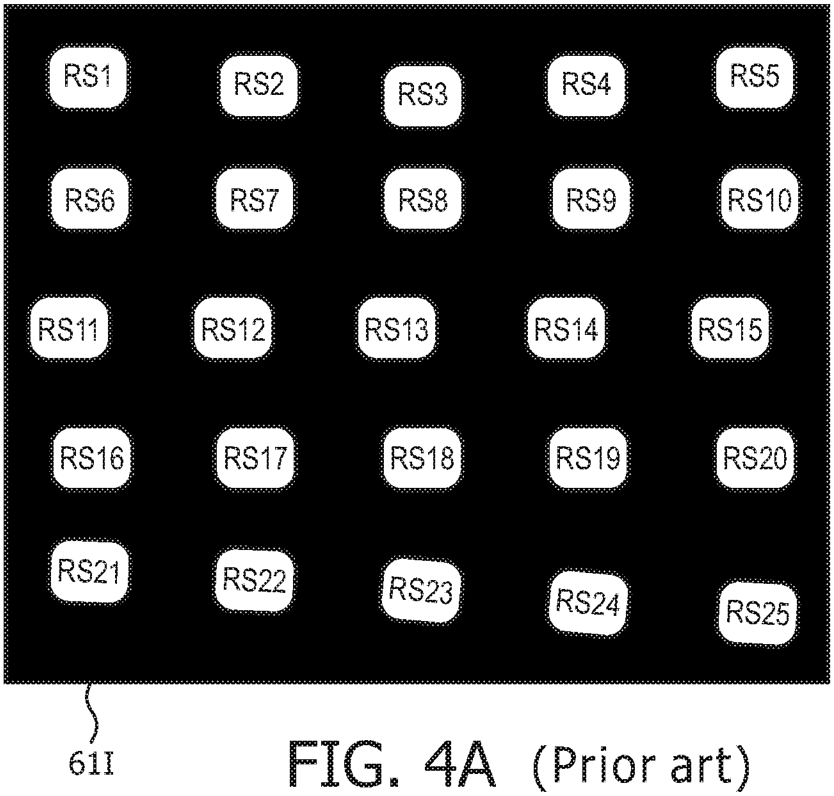
FIGS. 4A and 4B illustrate exemplary 2D views of brachytherapy seed distribution images as known in the art.
Figure 4B:
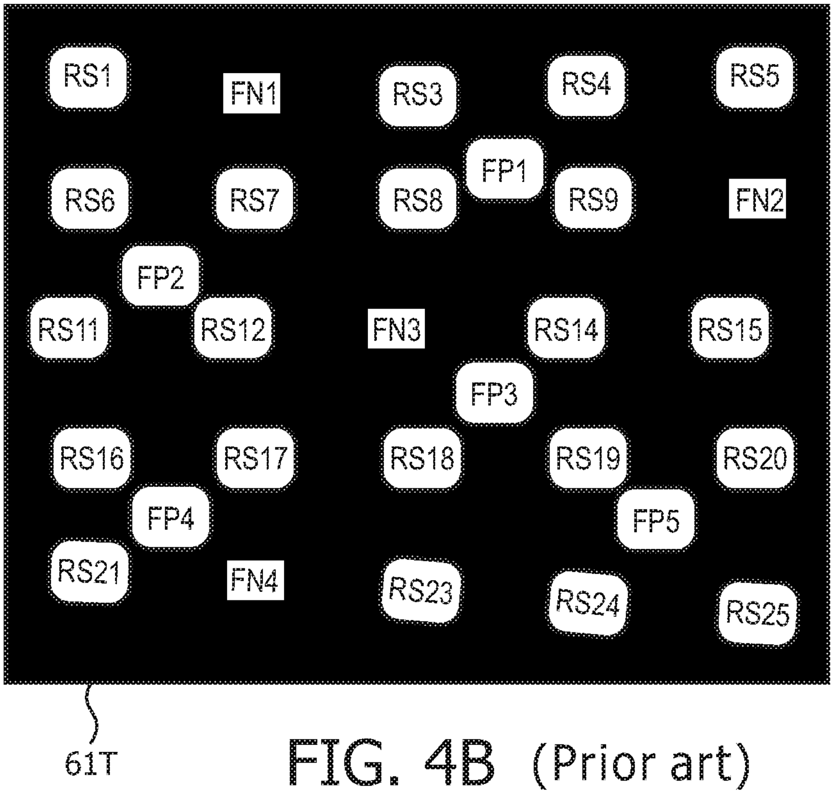
Figure 6:
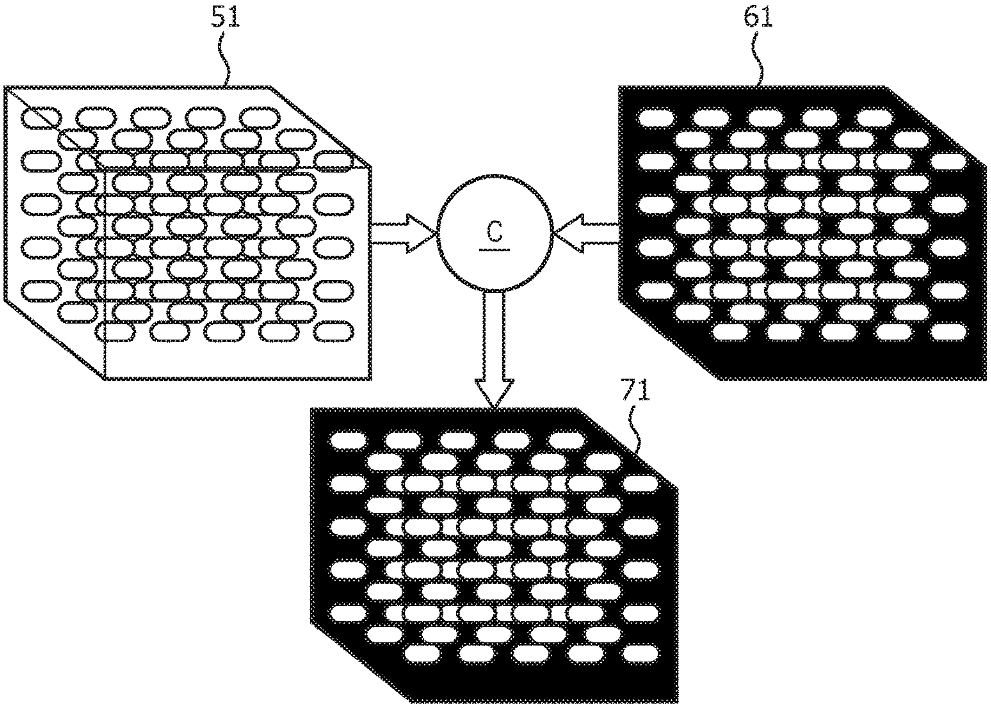
FIG. 6 illustrates an exemplary generation of a brachytherapy composite seed distribution in accordance with the present invention.
Figure 7:
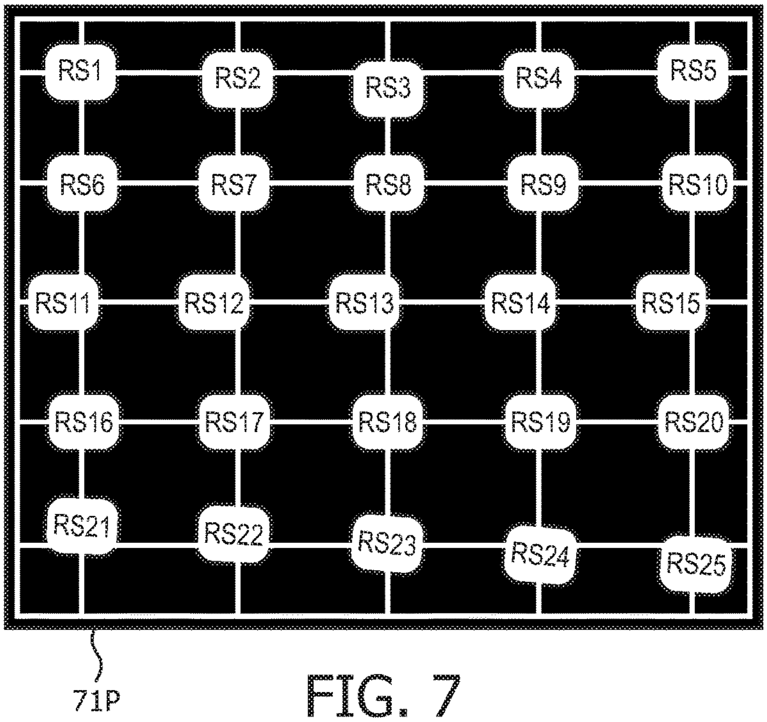
FIG. 7 illustrates an exemplary composite seed distribution map of FIG. 6.

For example, referring to FIG. 6, corresponding planar reviews 51T (FIG. 3B) and 61T (FIG. 4B) of respective tracked seed distribution map 51 and seed distribution image 61 are combined in a manner that (1) confirms projected locations of radioactive seeds RS1, RS3-RS9, RS11, RS12, RS14-RS21, and RS23-RS25 shown in planer view 61T of seed distribution image 61, (2) recovers false negative projected locations FN1-FN4 of radioactive seeds RS2, RS10, RS13 and RS22 shown in planer view 61T of seed distribution image 61, and (3) removes false positive projected locations FP1-FP5 shown in planer view 61T of seed distribution image 61. The result is the generation of planar view 71P of composite seed distribution map 71 of estimated locations as shown in FIG. 7 including (1) delivery locations of RS2, RS10, RS13 and RS22 shown in planar view 51T of tracked seed distribution map 51 for recovering false negative projected location(s) FN1-FN4 of radioactive seeds RS2, RS10, RS13 and RS22, and (2) projected locations of radioactive seeds RS1, RS3-RS9, RS11, RS12, RS14-RS21, and RS23-RS25 confirmed by the delivery locations of such radioactive seeds.

In one embodiment, a combination of the tracked seed distribution map and the seed distribution image involves an application by brachytherapy seed localizer 70 of a distance metric between tracked seed distribution map 51 and seed distribution image 61 for (1) confirming one or more of the projected locations of seed distribution image 61, (2) recovering any identified false negative projected location(s) of seed distribution image 61, and/or (3) removing any identified false positive projected location(s) from seed distribution image 61. More particularly, brachytherapy seed localizer 70 may generate a reconstructed seed distribution map of extracted projected locations from seed distribution image 61 and apply a distance metric between assignable pairs of radioactive seeds between reconstructed seed distribution map and tracked seed distribution map 51 to generate composite seed distribution map 71.

Figure 1:
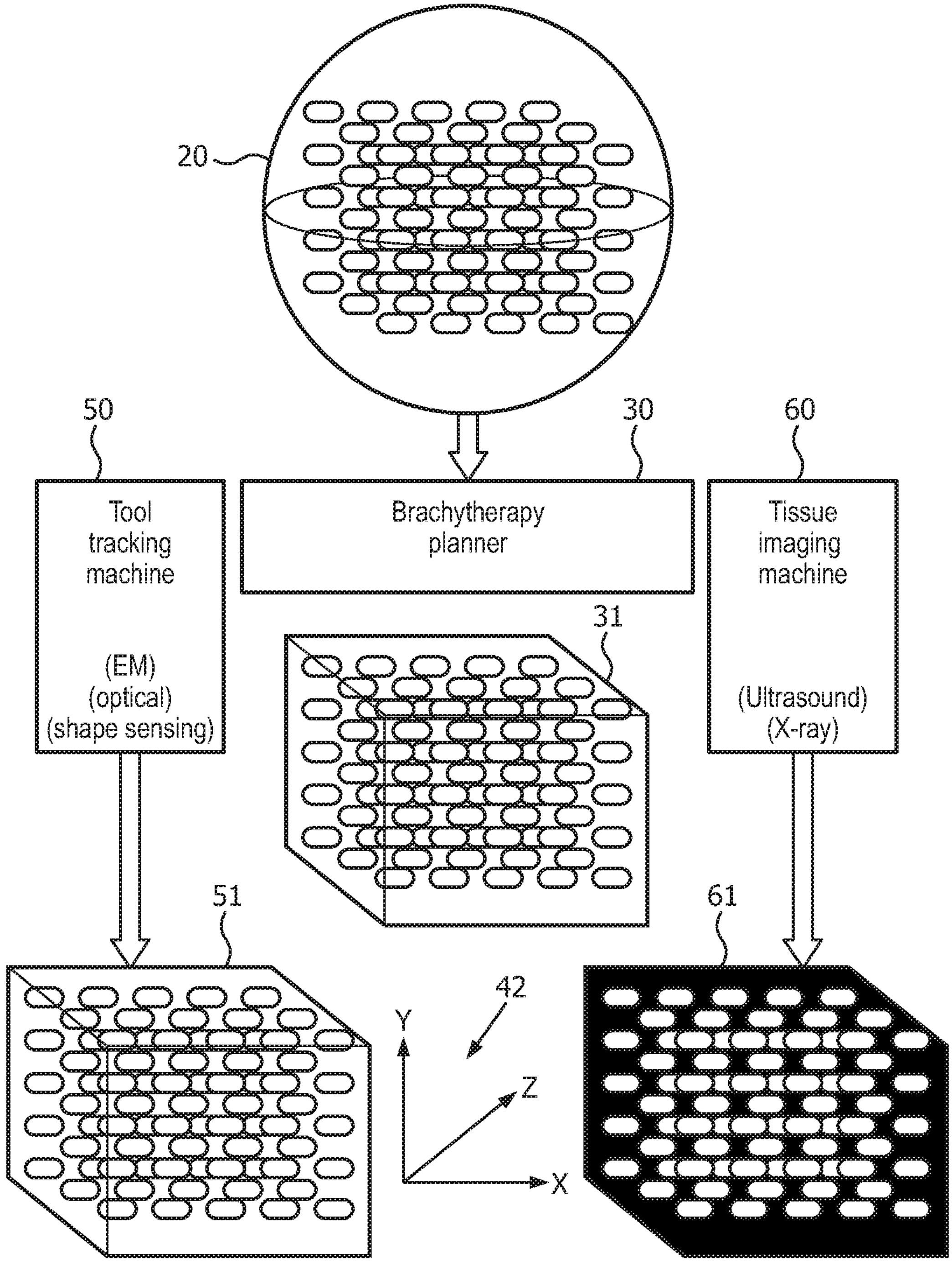
FIG. 1 illustrates an exemplary embodiment of a brachytherapy delivery system as known in the art.
Figure 2A:
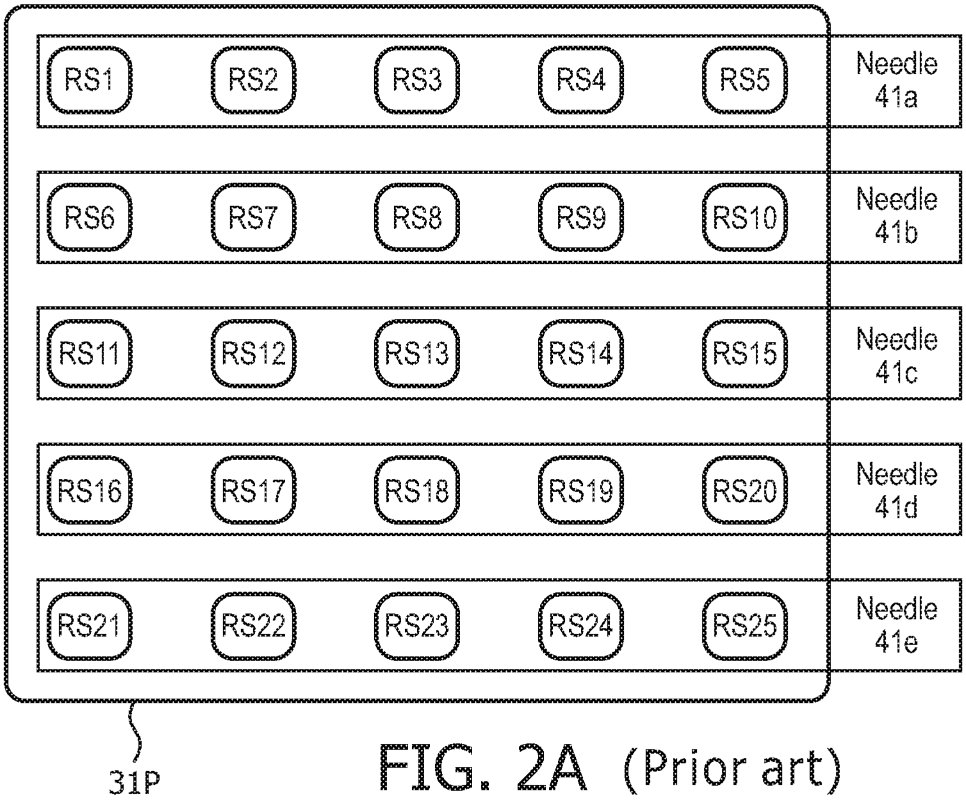
FIG. 2A illustrates an exemplary 2D view of a brachytherapy planned seed distribution map as known in the art.
Figure 2B:
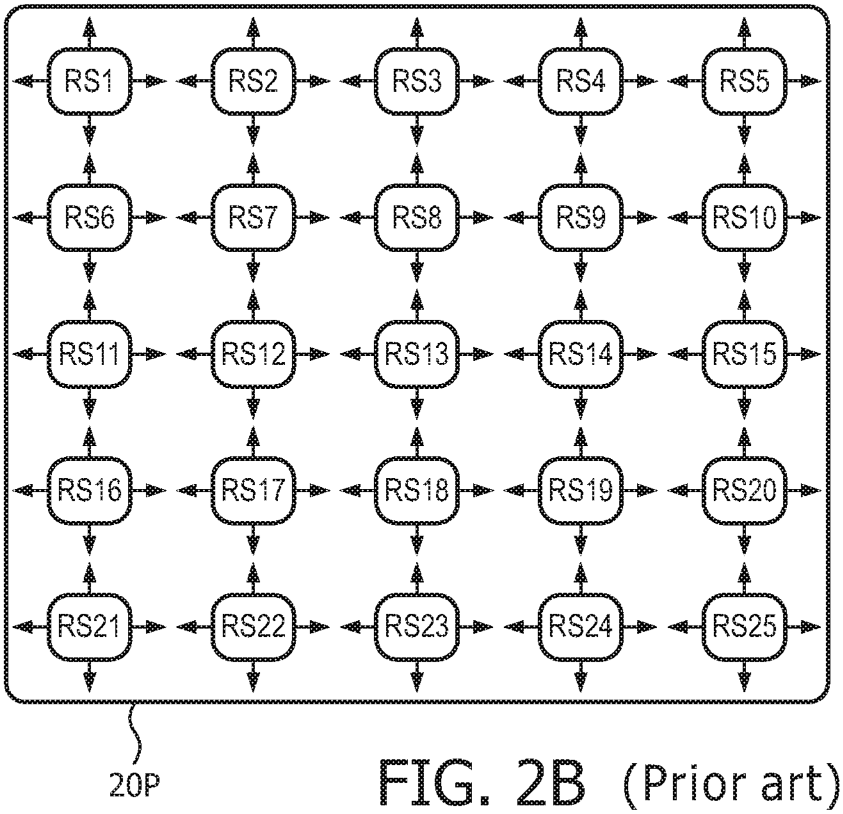
FIG. 2B illustrates an exemplary 2D views of various forces working on planned locations of the planned seed distribution map shown in FIG. 2A.

Exemplary embodiments of various methods of the present invention executable by the brachytherapy localization system of FIG. 5 will now be described herein to facilitate a further understanding of the present invention. While the various methods are described in the context of the planar view of maps/image shown in FIGS. 2-4, those having ordinary skill in the art will appreciate how to apply the various methods to brachytherapy procedures as known in the art, particularly for LDR brachytherapy.

Figure 8:
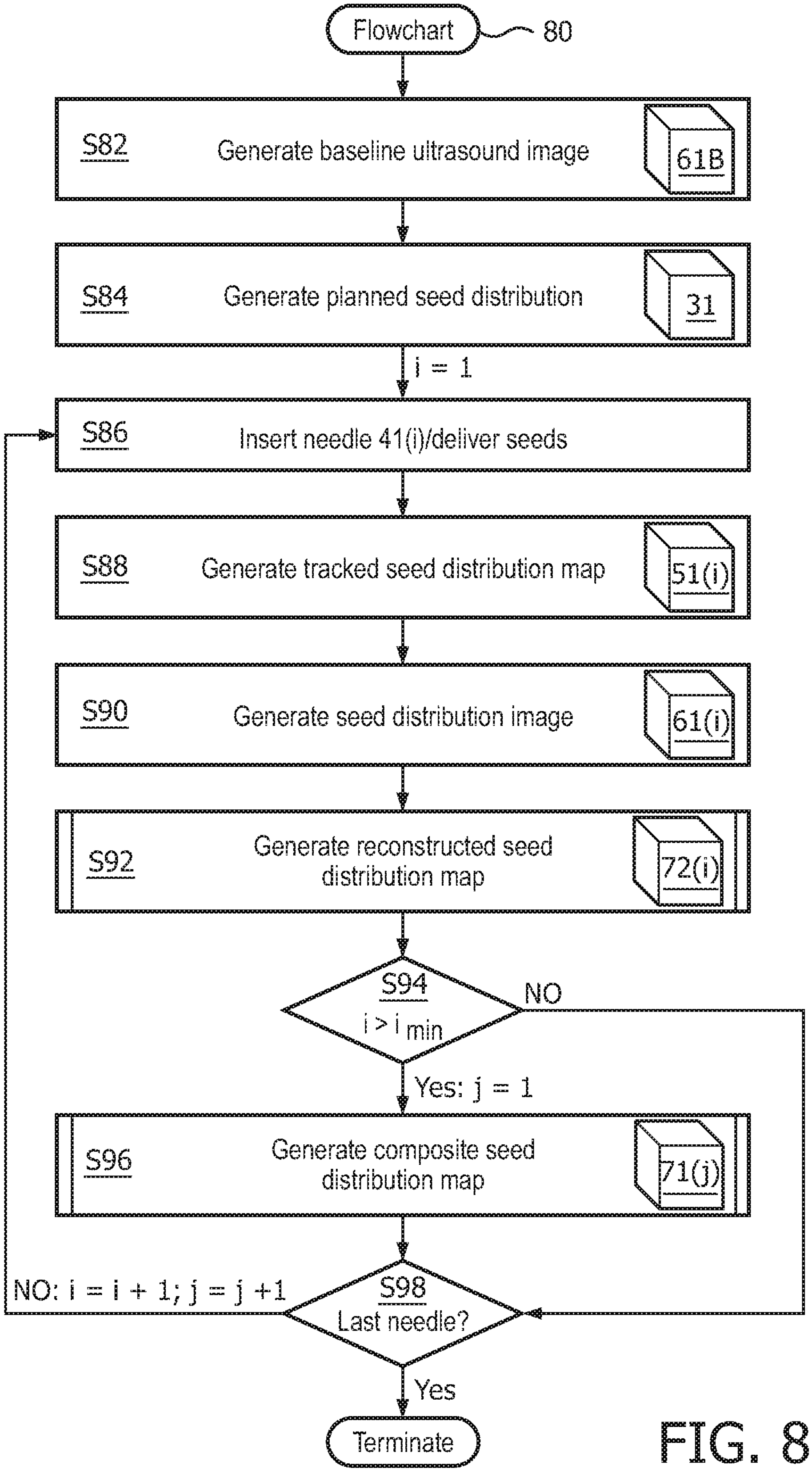
FIG. 8 illustrates a flowchart representative of an exemplary embodiment of a brachytherapy localization method in accordance with the present invention.

FIG. 8 illustrates a flowchart 80 representative of a brachytherapy localization method of the present invention in the context of utilizing five (5) applicator needles 41 with $i_{min}$ being four (4) applicator needles. Referring to FIGS. 5 and 8, a stage S82 of flowchart 80 encompasses a generation by ultrasound imaging machine 60 of a baseline ultrasound image 61B of diseased tissue 20 prior to any insertion of application needles 41, and a stage S84 of flowchart 80 encompasses a generation by brachytherapy planner 30 of planned seed distribution map 31 of radioactive seeds RS1-RS25 within diseased tissue 20.

A stage S86 of flowchart 80 encompasses an insertion of a first application needle 41(1) into diseased tissue 20 and a delivery by seed delivery system 40 of radioactive seeds RS1-RS5 in accordance with planned seed distribution map 31, and a stage S88 of flowchart 80 encompasses an electromagnetic tracking by electromagnetic tracking machine 50 of each delivery location of radioactive seed RS1-RS5 to thereby generate a delivery seed distribution map 51(1) by electromagnetic tracking machine 50 and/or brachytherapy localizer 70 of radioactive seeds RS1-RS5 delivered to diseased tissue 20.

A stage S90 of flowchart 80 encompasses a generation by ultrasound imaging machine 60 of a seed distribution image 61(1) of projected locations of radioactive seeds RS1-RS5 delivered by applicator needle 40(1) during stage S86, and a stage S92 of flowchart 80 encompasses a generation by brachytherapy localizer 70 of a reconstructed seed distribution map 72(1) of projected locations of radioactive seeds RS1-RS5 extracted from seed distribution image 61(1).

Flowchart 80 returns to stage S86 whereby a second application needle 41(2) is inserted into diseased tissue 20 and seed delivery system 40 delivers additional radioactive seeds RS6-RS10 in accordance with planned seed distribution map 31. Thereafter, stage S88 encompasses an electromagnetic tracking by electromagnetic tracking machine 50 of each delivery location of radioactive seeds RS6-RS10 delivered by applicator needle 41(2) to thereby generate a tracked seed distribution map 51(2) by electromagnetic tracking machine 50 and/or brachytherapy localizer 70 of all delivered radioactive seeds RS1-RS10 to diseased tissue 20.

Stage S90 encompasses a generation by ultrasound imaging machine 60 of a seed distribution image 61(2) of all delivered radioactive seeds RS1-RS10 delivered during a second iteration of stage S86, and stage S92 encompasses a generation by brachytherapy localizer 70 of a reconstructed seed distribution map 72(2) of projected locations of all radioactive seeds RS1-RS10 extracted from seed distribution images 61(1) and 61(2).

Figure 9:
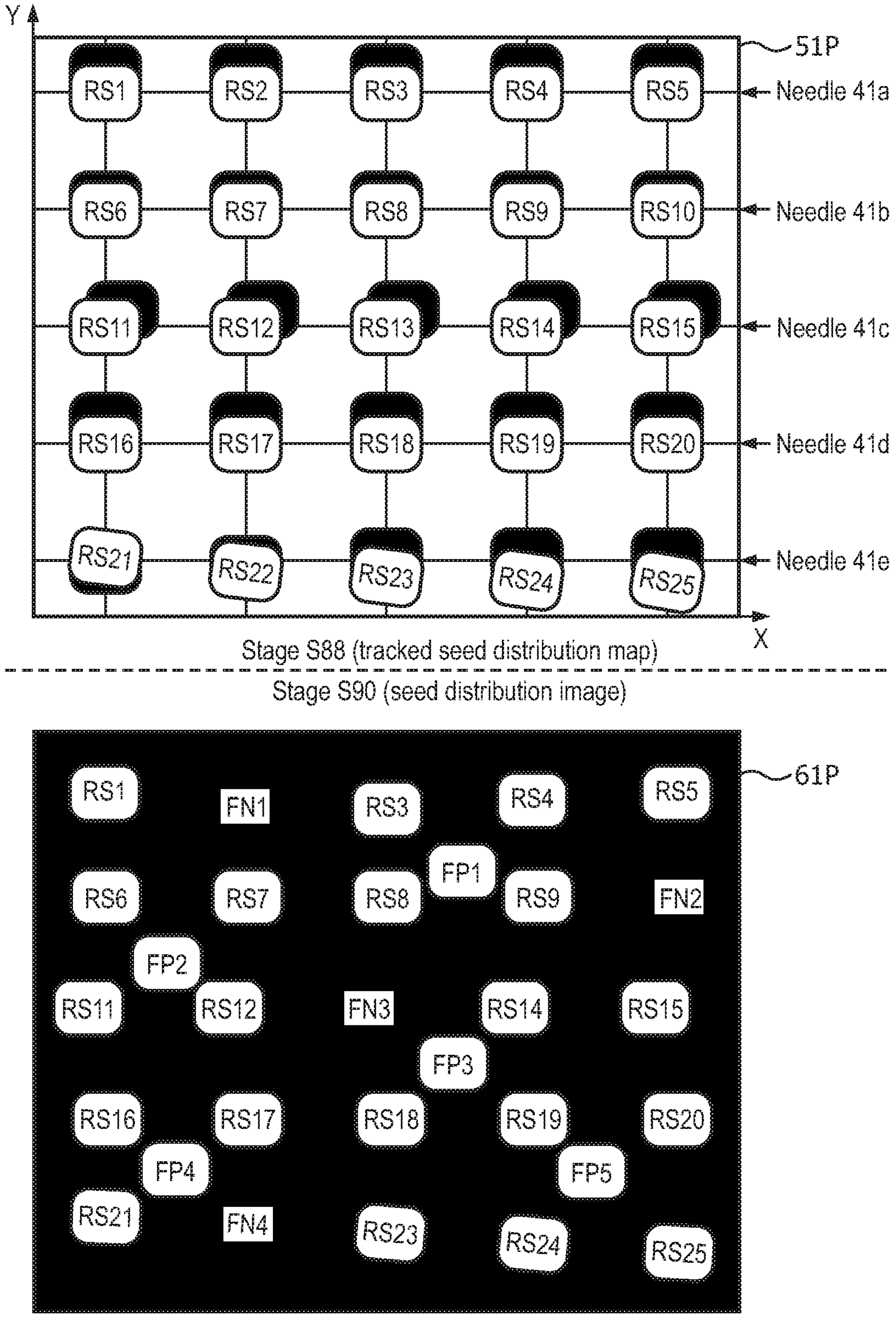
FIG. 9 illustrates exemplary generations of a tracked seed distribution map and an image seed distribution map in accordance with the flowchart illustrated in FIG. 8.
Figure 10:
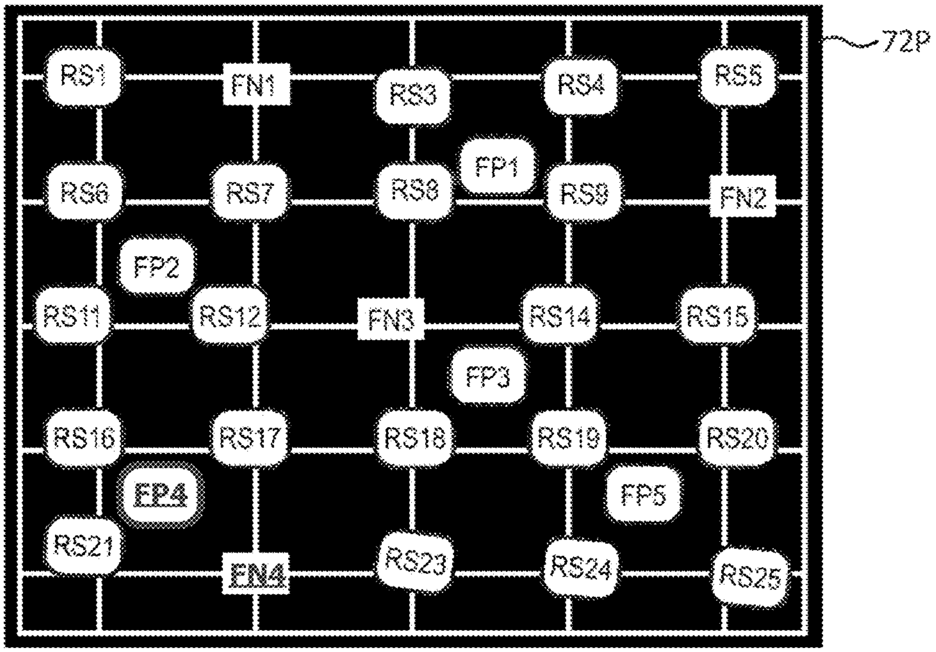
FIG. 10 illustrates an exemplary generation of a reconstruction seed distribution map and a composite seed distribution map in accordance with the flowchart illustrated in FIG. 8.
Figure 10:
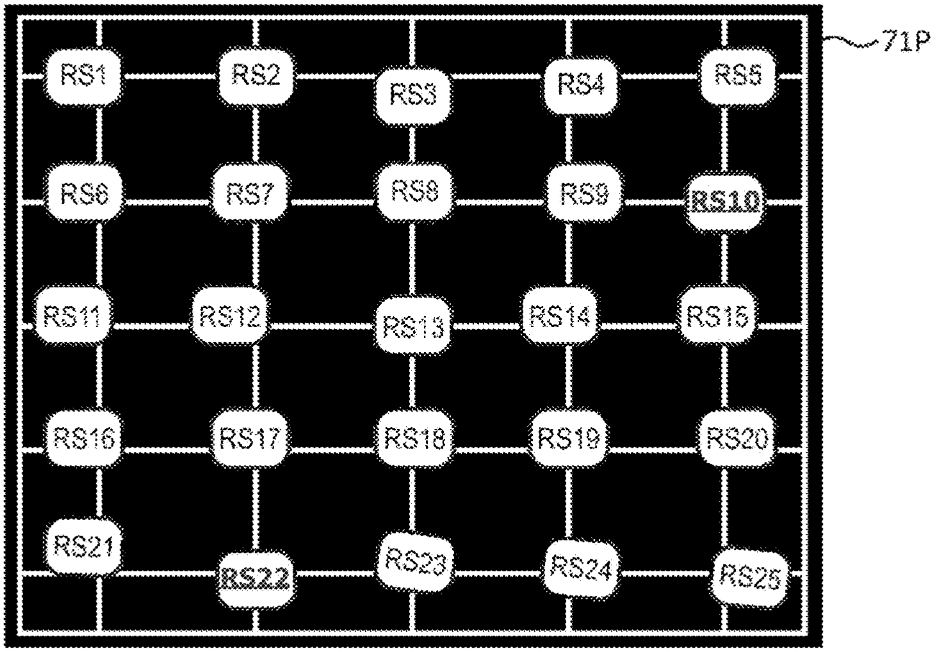

With min being four (4) applicator needles 41, stages S86-S92 will be repeated through three (3) more cycle resulting in tracked seed distribution map 51 having a planar view 51P as exemplary shown in FIG. 9, seed distribution image 61 having a planar view 61P as exemplary shown in FIG. 9, and reconstructed seed distribution map 72 having a planar view 72P as exemplary shown in FIG. 10.

Upon the fifth generation of reconstructed seed distribution map 72, a stage S96 of flowchart 90 encompasses generation by brachytherapy localizer 70 of a composite seed distribution map 71(1) of radioactive seeds within diseased tissue 20 derived from a combination of a tracked seed distribution map 51(5) and a reconstructed seed distribution map 72(5). More particularly; the combination confirms accurate projected locations of radioactive seeds RS1, RS3-RS9, RS11, RS12, RS14-RS21 and RS23-R25 within reconstructed seed distribution map 72. The combination further identifies false negative projected locations FN1-FN4 within reconstructed seed distribution map 72 and recovers locations of radioactive seeds RS2, RS10, RS13 and RS-22 from tracked seed distribution map 51. The combination also identifies and removes false positive projected location(s) FM-FP5 within reconstructed seed distribution map 72.

Upon termination of flowchart 80, composite seed distribution map 71 having a planar view 71P as exemplary shown in FIG. 10 provides intra-procedural feedback implemented during stage S96 based on accuracy achievable by ultrasound seed localization implemented by stages S90 and S92 with a robustness of electromagnetic tracking localization implemented by stage S88. This intra-procedural feedback is utilized by brachytherapy planner 30 and/or or brachytherapy localizer 70 for estimating a radioactive dose distribution of the radioactive seeds within the diseased tissue as a function of the composite seed distribution map as known in the art. In one embodiment, the estimated radioactive dose estimation may be displayed in any applicable form including, but not limited to, a superimposition of markers on the most current ultrasound image of the diseased tissue and a 2D/3D rendering of the composite seed distribution map and/or the estimated radioactive dose distribution.

Still referring to FIG. 8, in practice, stage S94 may occur between stages S88 and S90, between stages S90 and S92, or between stages S92 and S96. Also in practice, stage S92 may or may not involve a removal of artifact(s) within reconstructed seed distribution map(s) 72 as will be further explained herein in connection with a description of FIG. 13.

Exemplary embodiments of brachytherapy localizer 70 and stages S92 and S96 of flowchart 80 will now be described herein.

Figure 11:
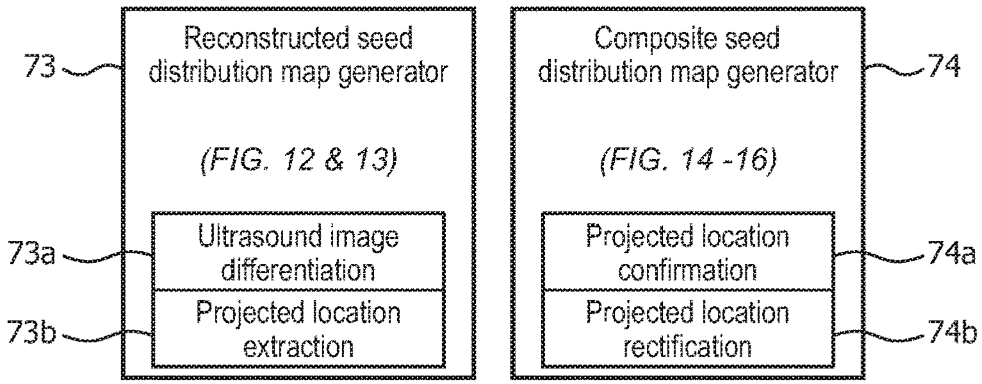
FIG. 11 illustrates an exemplary modular network of a brachytherapy localizer illustrated in FIG. 5.

FIG. 11 illustrates a software modular network for brachytherapy localizer 70 having a reconstructed seed distribution map generator 73 and a composite seed distribution map generator 74.

Figure 12:
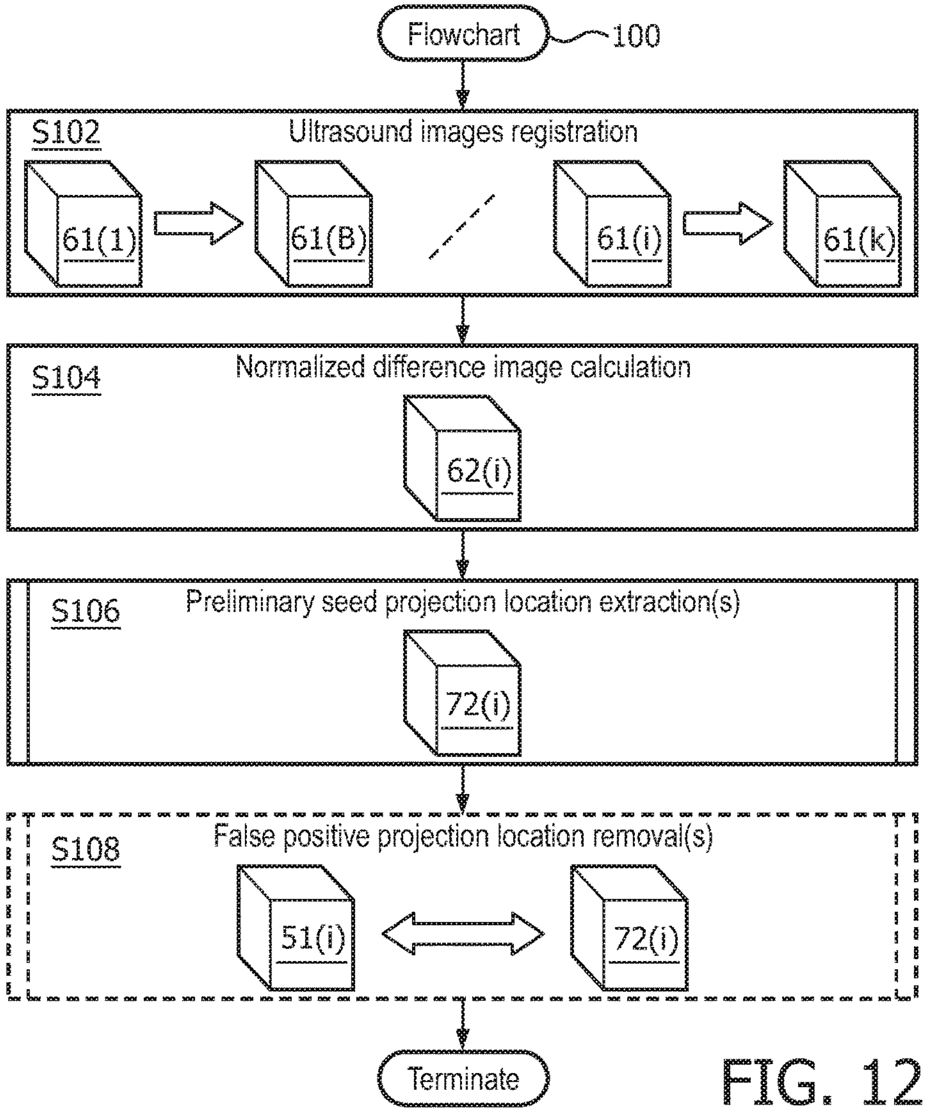
FIG. 12 illustrates a flowchart representative of an exemplary embodiment of a reconstruction seed distribution map generation method in accordance with the present invention.

Reconstruction seed distribution map generator 73 is a software module programmed with an ultrasound image differentiation routine 73*a* and a projected location extraction routine 73*b* for executing a flowchart 100 of FIG. 12 during stage S92 (FIG. 8) for purposes of generating reconstruction seed distribution map 72.

Referring to FIG. 12, a stage S102 of flowchart 100 encompasses ultrasound image differentiation routine 73*a* registering sequentially generated seed distribution images 61 of diseased tissue 20, and a stage S104 of flowchart 100 encompasses ultrasound image differentiation routine 73*a* calculating a normalized ultrasound difference image 62(*i*)

for the current registered seed distribution images 61. With the first execution of stage S102, ultrasound image differentiation routine 73*a* registers seed distribution image 61(1) to baseline ultrasound image 61B (e.g., an elastic registration: Demon's algorithm). Subsequent executions of stage S102 involve ultrasound image differentiation routine 73*a* registering a current seed distribution image 61(*i*) to a preceding seed distribution image 61(*k*), with k=i−1.

Still referring to FIG. 12, a stage S106 of flowchart 100 encompasses projected location extraction routine 73*b* extracting projected location(s) for each radioactive seed sufficiently visible within the current ultrasound difference image 62(*i*). In one embodiment of stage S106, projected location extraction routine 73*b* executes a flowchart 110 of FIG. 13 representative of a projected location extraction method of the present invention.

Figure 13:
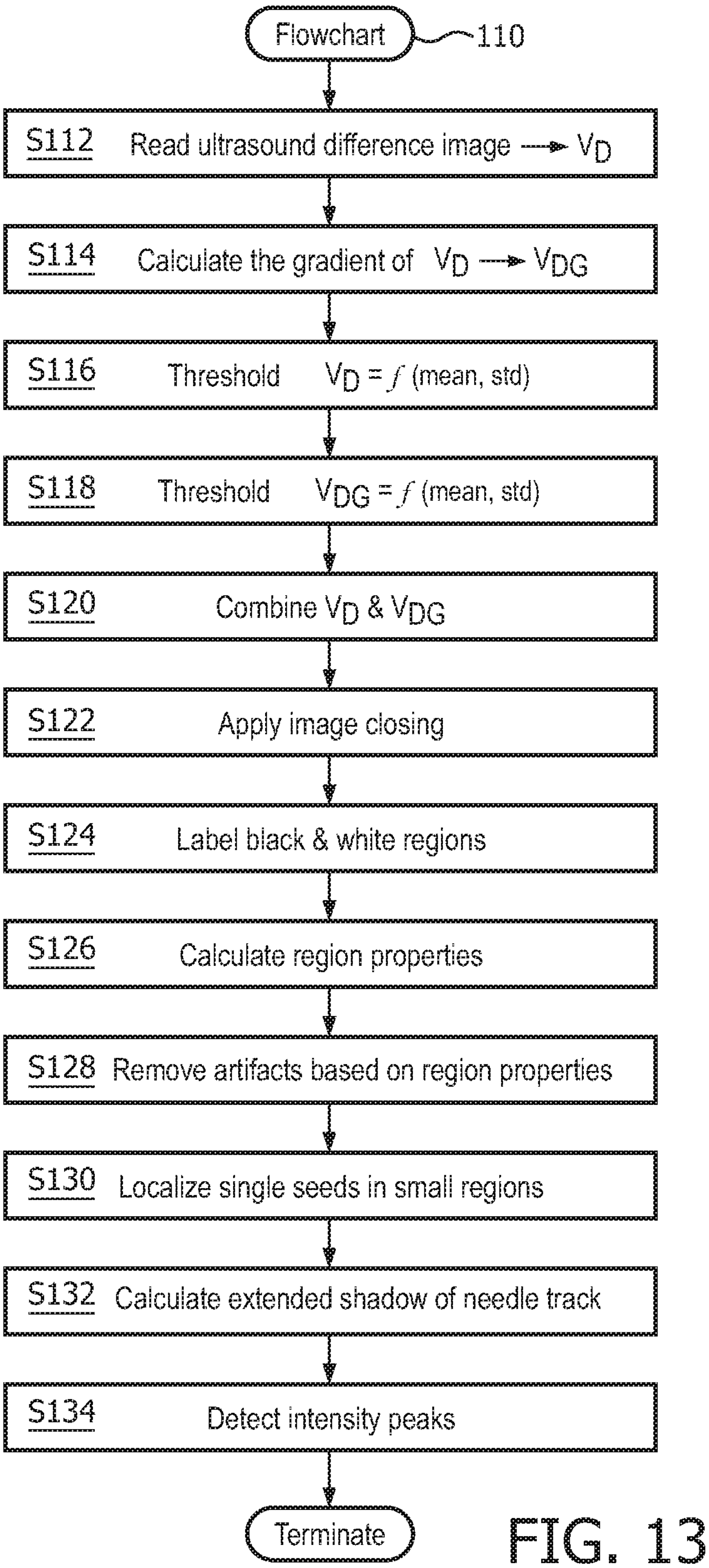
FIG. 13 illustrates a flowchart representative of an exemplary embodiment of a projected location extraction method in accordance with the present invention.

Referring to FIG. 13, stages S112-S134 of flowchart 110 encompass projected location extraction routine 73*b:* reading pixel intensities $V_d$ of current ultrasound difference image 62(*i*) (S112);

calculating a gradient $V_{dg}$ of pixel intensities $V_d$ (S114);

applying a binary threshold to pixel intensities $V_d$ based on a mean and standard deviation of pixel intensities $V_d$ (S116);

binary thresholding gradient $V_{dg}$ based on a mean and standard deviation of gradient $V_{dg}$ (S118);

combing of pixel intensities $V_d$ and gradient $V_{dg}$ (S120);

applying an image closing (S122);

labeling black and white regions (S124);

calculating region properties (S126);

removing artifacts based on region properties (S128);

localizing single seeds in small regions (S130);

calculating extended shadow of needle tracks (S132); and detecting intensity peaks (S134).

Those having ordinary skill in the art will appreciate how to implement an execution of S112-S134.

Referring back to FIG. 12, flowchart 100 includes an optional stage S108 for removing any false positive projection location(s) from reconstructed seed distribution map 72 on an individual needle basis. In one embodiment of stage S108, any false positive projection location(s) within reconstructed seed distribution map 72 are identified and removed by executing a Hungarian algorithm as known in the art involving a comparison electromagnetic tracked delivery locations of seeds and the ultrasound image projected locations for that needle alone. Upon termination of flowchart 110, a reconstructed seed distribution map 72 will include extracted projected locations of radioactive seeds within diseased tissue 20, and may include false projected locations as exemplary shown in planar view 72P of FIG. 10.

Figure 14:
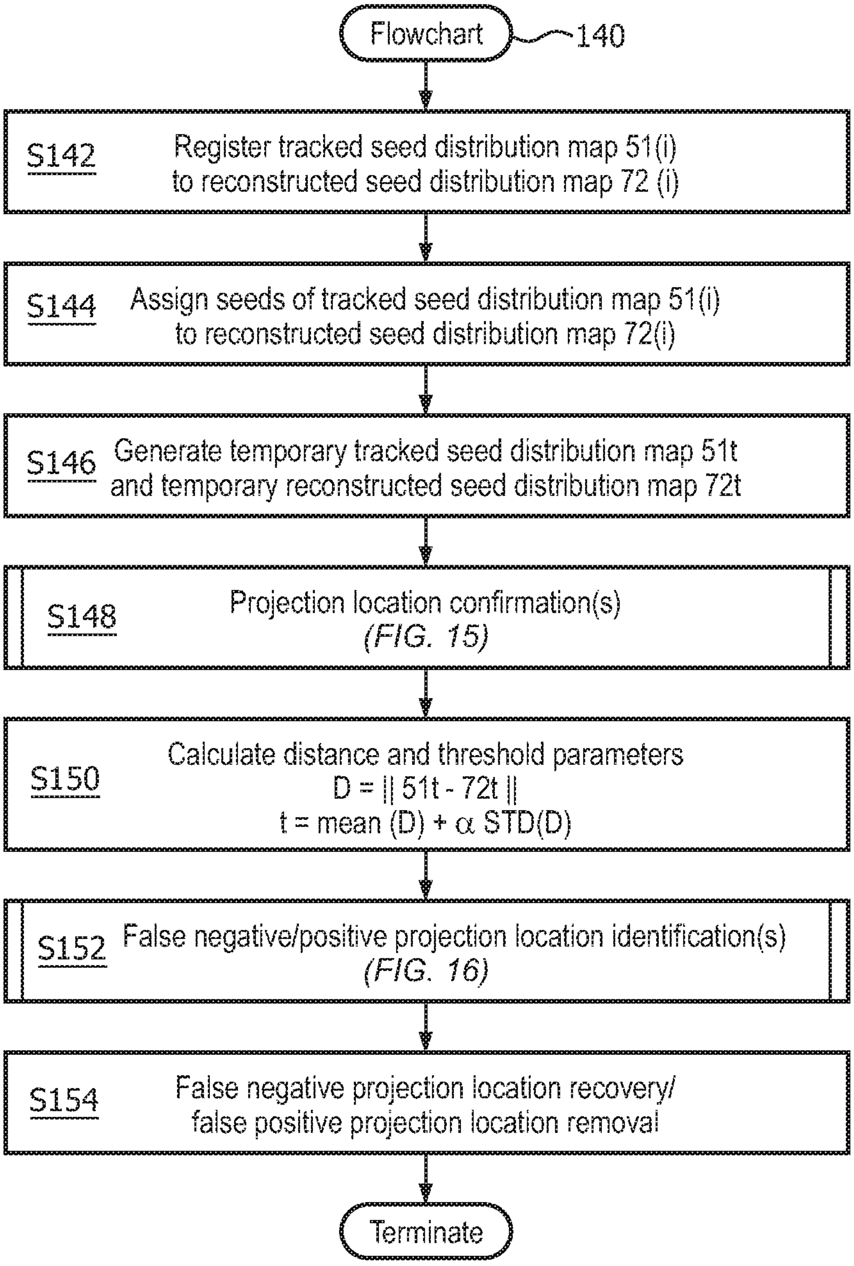
FIG. 14 illustrates a flowchart representative of an exemplary embodiment of a composite seed distribution map generation method in accordance with the present invention.

Referring back to FIG. 11, composite seed distribution map generator 74 is a software module programmed with projected location confirmation routine 74*a* and a projected location rectification routine 74*b* for executing a flowchart 140 of FIG. 14 during stage S96 (FIG. 8) for purposes of generating composite seed distribution map 71.

Referring to FIG. 14, a stage S142 of flowchart 140 encompasses projected location confirmation routine 74*a* registering a current tracked seed distribution map 51(*i*) to a current reconstructed seed distribution map 72(*i*), and a stage S144 of flowchart 140 encompasses projected location confirmation routine 74*a* assigning each delivered location of the radioactive seeds within the current tracked seed distribution map 51(*i*) to any corresponding projected location within reconstructed seed distribution map 72(*i*). For example, referring to respective planar views 51P and 72P of FIGS. 9 and 10, radioactive seeds RS1, RS3-RS9, RS11, RS12, RS14-RS21 and RS23-RS25 of tracked seed distribution map 51 would be assigned to respective radioactive seeds RS1, RS3-RS9, RS11, RS12, RS14-RS21 and RS23-RS25 of reconstructed seed distribution map 72.

A stage S146 of flowchart 140 encompasses projected location confirmation routine 74*a* generating a temporary tracked seed distribution map 51*t* and a temporary reconstructed seed distribution map 72*t* as respective duplicates of the current tracked seed distribution map 51(*i*) and reconstructed seed distribution map 72(*i*).

A stage S148 of flowchart 140 encompasses projected location confirmation routine 74*a* confirming one or more of the projected locations of radioactive seeds previously identified within the current reconstructed seed distribution map 72(*i*). In one embodiment of stage S148, projected location confirmation routine 74*a* implements a flowchart 160 of FIG. 15 representative of a projected location confirmation method of the present invention.

Figure 15:
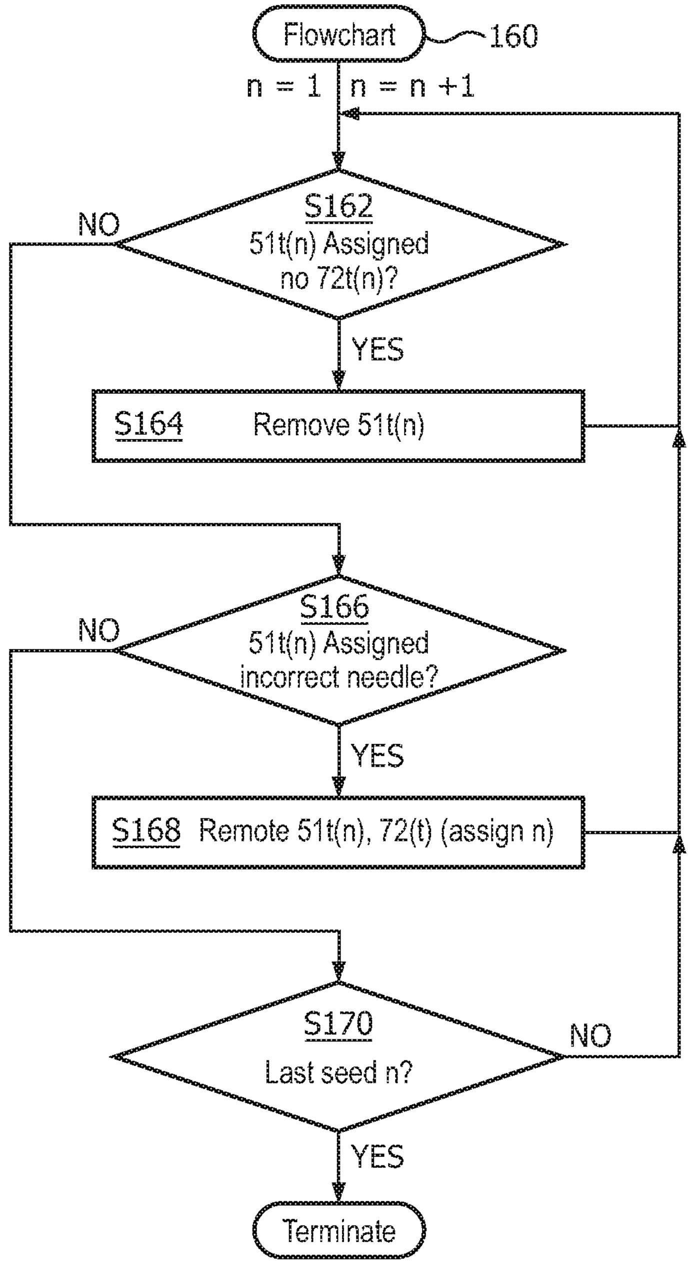
FIG. 15 illustrates a flowchart representative of an exemplary embodiment of a projected location confirmation method in accordance with the present invention.

Referring to FIG. 15, stages S162-S170 of flowchart 160 are executed by projected location confirmation routine 74*a* for each radioactive seed for a total number n of delivered radioactive seeds. Stage S162 encompasses projected location confirmation routine 74*a* determining if a particular radioactive seed 51*t*(*n*) within temporary tracked seed distribution map 51*t* has not been assigned to a radioactive seed 72*t*(*n*) within temporary reconstructed seed distribution map 72*t*. If yes, then that particular radioactive seed 51*t*(*n*) is removed from temporary tracked seed distribution map 51*t* during stage S164. Otherwise if no, stage S166 encompasses projected-location confirmation routine 74*a* determining if the radioactive seed. 51*t*(*n*) has been assigned to an incorrect applicator needle 41. If yes, then that particular radioactive seed 51*t*(*n*) and assigned radioactive seed 72*t*(*n*) are removed respectively from temporary tracked seed distribution map 51*t* and temporary reconstructed seed distribution map 72*t* during stage S168. Otherwise if not, then that particular radioactive seed 51*t*(*n*) confirms the location of assigned radioactive seed 72*t*(*n*) within temporary reconstructed seed distribution map 72*t* and stages S162-S170 are repeated accordingly for any remaining radioactive seeds n.

By example, a full execution of flowchart 160 would result in a removal of radioactive seeds RS2, RS10, RS13 and RS22 from the temporary version of tracked seed distribution map 51 as exemplary shown in planar view 51P in FIG. 9, and a confirmation of projected locations of radioactive seeds RS1, RS3-RS9, RS11, RS12, RS14-RS21 and RS23-RS25 within the temporary version of reconstructed seed distribution map 72 as exemplary shown in planar view 72P in FIG. 10.

Referring back to FIG. 14, a stage S150 of flowchart 140 encompasses projected location confirmation routine 74*a* calculating of a set of 3D spatial distance values D in accordance with D=||51*t*−73*t*|| and a distance threshold T in accordance with T=mean(D)+α STD(D), where α is an adjustable factor (e.g., 3) for utilizing more of projected locations of reconstructed seed distribution map 72*t* (e.g., >3), or more of the delivery locations of tracked seed distribution map 51*t* (i.e., <3).

A stage S152 of flowchart 140 encompasses an identification of any false projected locations within the current reconstructed seed distribution map 72(*i*). In one embodiment of stage S152, projected location rectification routine 74*b* implements a flowchart 180 of FIG. 16 representative of a false projected location removal/recovery method of the present invention.

Figure 16:
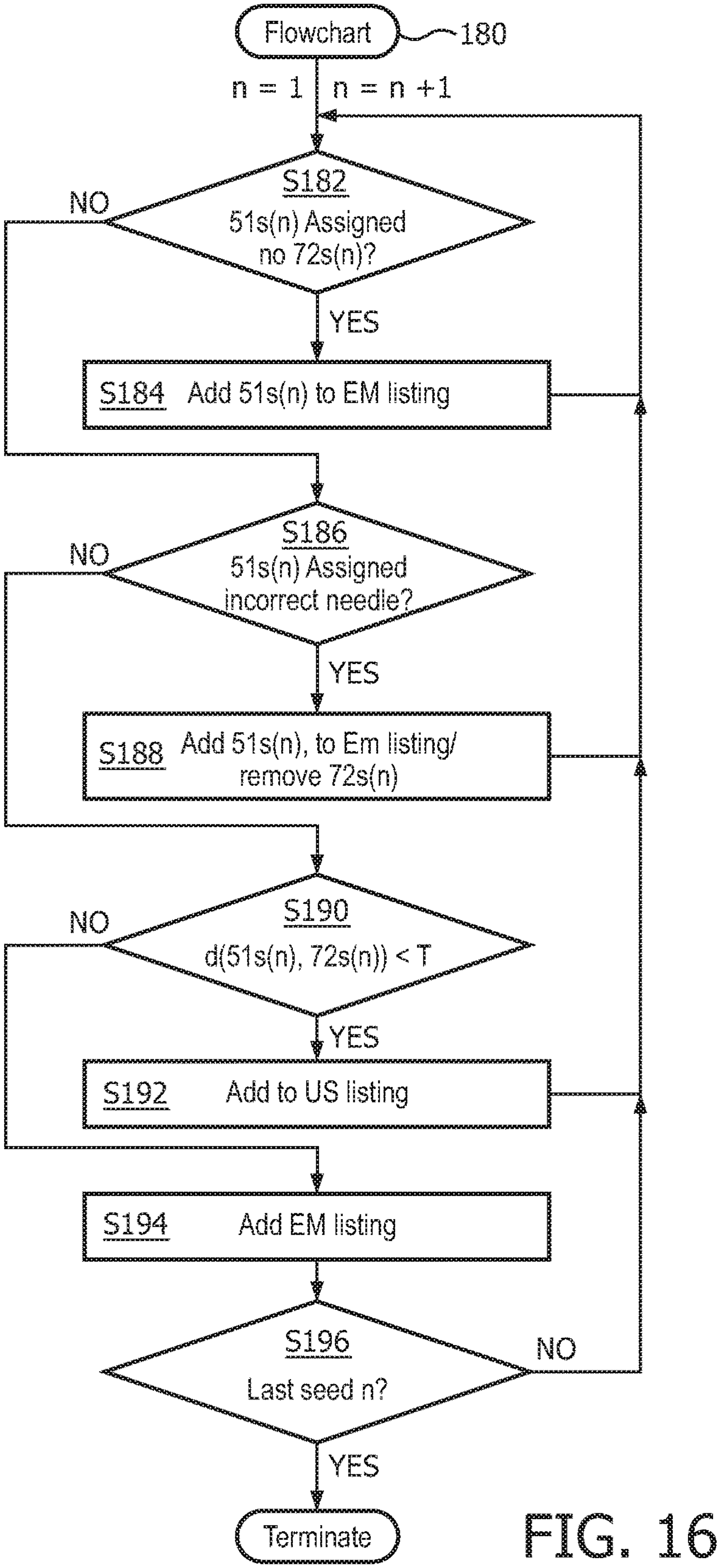
FIG. 16 illustrates a flowchart representative of an exemplary embodiment of a false projected location removal/recovery method in accordance with the present invention.

Referring to FIG. 16, stages S182-S186 are executed by projected location rectification routine 74*b* for each radioactive seed for a total number n of delivered radioactive seeds. Stage S182 encompasses projected location rectification routine 74*b* determining if a particular radioactive seed 51*s*(*n*) within current tracked seed distribution map 51(*i*) has not been assigned to a radioactive seed 72*s*(*n*) within reconstructed seed distribution map 72(*i*). If yes, then projected location rectification routine 74*b* adds that particular radioactive seed 51*s*(*n*) to an electromagnetic ("EM") listing during stage S184. Otherwise if no, stage S186 encompasses projected location rectification routine 74*b* determining if the radioactive seed 51*s*(*n*) has been assigned to an incorrect applicator needle 41. If yes, then projected location rectification routine 74*b* adds that particular radioactive seed 51*s*(*n*) to the EM listing and the assigned radioactive seed 72*s*(*n*) is removed from current reconstructed seed distribution map 72(*i*).

Otherwise if not, stage S190 encompasses projected location rectification routine 74*b* calculating a seed distance d between radioactive seeds 51*s*(*n*) and 72*s*(*n*) and a comparison of seed distance d to the previously calculated threshold T of stage S150 (FIG. 13). If seed distance d is less than threshold T, then stage S192 encompasses projected location rectification routine 74*b* adding the radioactive seeds 51*s*(*n*) to an ultrasound ("US") listing. Otherwise if seed distance d is greater than or equal to threshold T, then stage S194 encompasses projected location rectification routine 74*b* adding the radioactive seeds 51*s*(*n*) to the EM listing. Stages S182-S194 are repeated accordingly for any remaining radioactive seeds n.

Upon completion of flowchart 180, the EM listing will identify seed locations that should be estimated based on the delivery locations of tracked seed distribution map 51(*i*), and the US listing will identify seed locations that should be estimated using the projected locations of reconstructed seed distribution map 72(*i*) (i.e. the "correct projected location of radioactive seeds", after removal of false positive projected locations of radioactive seeds). Note that each radioactive seed n can now be found either on the EM listing or on the US listing.

Referring back to FIG. 14, a stage S154 of flowchart 140 encompasses a recovery by projected location rectification routine 74*b* of all identified false negative projected location for cumulative reconstructed seed distribution map 72(*i*) and encompasses a removal by projected location rectification routine 74*b* of all identified false positive projected locations within the cumulative reconstructed seed distribution map 72(*i*). The result is a composite seed distribution map 71(*j*), such as, for example, planar view 71P of composite seed distribution map 71 shown in FIG. 10.

In one embodiment of stage S154 as related to the EM listing and the US listing of flowchart 180 (FIG. 16), for all seeds found on the US listing (i.e. the correct projected locations), the corresponding delivery seed locations are registered to the projected seed locations, resulting in a registration transformation T. The same transformation T is then applied to the delivery locations of all seeds on the EM listing, which results in delivery location estimates mapped into the ultrasound space. Finally, a combined seed distribution map 71(*j*) is created by combining the projected locations from the radioactive seeds on the US listing with the delivery locations mapped into ultrasound space for the radioactive seeds from the EM listing. Again, result is a composite seed distribution map 71(*j*), such as, for example, the planar view 71P of composite seed distribution map 71 shown in FIG. 10.

Referring to FIGS. 5-16, those having ordinary skill in the art will appreciate numerous benefits of the present invention including, but not limited to, an intra-procedural feedback of a brachytherapy procedure based on combining an accuracy achievable by ultrasound seed localization with a robustness of electromagnetic tracking localization.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A brachytherapy seed localization system for localizing radioactive seeds within an ultrasound space of a diseased tissue, the brachytherapy seed localization system comprising:

a tool tracking machine configured to generate a tracked seed distribution map of delivered locations of the radioactive seeds within the ultrasound space of the diseased tissue; a tissue imaging machine configured to generate a seed distribution image of projected locations of the radioactive seeds within the ultrasound space of the diseased tissue, wherein the seed distribution image includes at least one false projected location of a radioactive seed within the ultrasound space of the diseased tissue; and a brachytherapy seed localizer configured to be in communication with the tool tracking machine and the tissue imaging machine, wherein, responsive to a reception of the tracked seed distribution map and the seed distribution image, the brachytherapy seed localizer is configured to generate a composite seed distribution map of estimated locations of the radioactive seeds within the ultrasound space of the diseased tissue derived from a combination of the tracked seed distribution map and the seed distribution image, the combination including an exclusion of the at least one false projected location of the radioactive seed within the ultrasound space of the diseased tissue from the composite seed distribution map.

2. The brachytherapy seed localization system of claim 1, wherein the composite seed distribution map is generated as a function of a distance metric between the tracked seed distribution map and the seed distribution image.

3. The brachytherapy seed localization system of claim 2, wherein the estimated locations of the radioactive seeds within the ultrasound space of the diseased tissue include at least one of the delivered locations of the radioactive seeds within the ultrasound space of the diseased tissue and at least one of the projected locations of the radioactive seeds within the ultrasound space of the diseased tissue as a function of the distance metric between the tracked seed distribution map and the seed distribution image.

4. The brachytherapy seed localization system of claim 2, wherein the estimated locations of the radioactive seeds within the ultrasound space of the diseased tissue exclusively include the delivered locations of the radioactive seeds within the ultrasound space of the diseased tissue as a function of the distance metric between the tracked seed distribution map and the seed distribution image.

5. The brachytherapy seed localization system of claim 2, wherein the estimated locations of the radioactive seeds within the ultrasound space of the diseased tissue exclusively include the projected locations of the radioactive seeds within the ultrasound space of the diseased tissue excluding the at least one false projected location of the radioactive seed within the ultrasound space of the diseased tissue as a function of the distance metric between the tracked seed distribution map and the seed distribution image.

6. The brachytherapy seed localization system of claim 1, wherein the brachytherapy seed localizer includes:

a reconstructed seed distribution map generator configured to generate a reconstructed seed distribution map of projected locations of the radioactive seeds within the ultrasound space of the diseased tissue extracted from the seed distribution image.

7. The brachytherapy seed localization system of claim 6, wherein the brachytherapy seed localizer includes:

a composite seed distribution map generator configured to generate the composite seed distribution map as a function of a distance metric between the tracked seed distribution map and the reconstructed seed distribution map.

8. The brachytherapy seed localization system of claim 7, wherein the estimated locations of the radioactive seeds within the ultrasound space of the diseased tissue include at least one of the delivered locations of the radioactive seeds within the ultrasound space of the diseased tissue and at least one of the projected locations of the radioactive seeds within the ultrasound space of the diseased tissue as a function of the distance metric between the tracked seed distribution map and the reconstructed seed distribution map.

9. The brachytherapy seed localization system of claim 7, wherein the estimated locations of the radioactive seeds within the ultrasound space of the diseased tissue exclusively include the delivered locations of the radioactive seeds within the ultrasound space of the diseased tissue as a function of the distance metric between the tracked seed distribution map and the reconstructed seed distribution map.

10. The brachytherapy seed localization system of claim 7, wherein the estimated locations of the radioactive seeds within the ultrasound space of the diseased tissue exclusively include the projected locations of the radioactive seeds within the ultrasound space of the diseased tissue excluding the at least one false projected location of the radioactive seed within the ultrasound space of the diseased tissue as a function of the distance metric between the tracked seed distribution map and the reconstructed seed distribution map.

11. A brachytherapy seed localizer for localizing radioactive seeds within an ultrasound space of a diseased tissue, the brachytherapy seed localizer comprising:

a reconstructed seed distribution map generator configured to generate a reconstructed seed distribution map of projected locations of the radioactive seeds within the ultrasound space of the diseased tissue extracted from a seed distribution image of projected locations of the radioactive seeds within the ultrasound space of the diseased tissue, wherein the reconstructed seed distribution image includes at least one false projected location of a radioactive seed within the ultrasound space of the diseased tissue; and a composite seed distribution map generator configured to be in communication with the reconstructed seed distribution map generator, wherein, in response to a reception of the reconstructed seed distribution map, the composite seed distribution map generator is configured to generate a composite seed distribution map of estimated locations of the radioactive seeds within the ultrasound space of the diseased tissue derived from a combination of a tracked seed distribution map of delivered locations of the radioactive seeds within the ultrasound space of the diseased tissue and the reconstructed seed distribution map of the radioactive seeds within the ultrasound space of the diseased tissue, the combination including an exclusion of the at least one false projected location of the radioactive seed within the ultrasound space of the diseased tissue from the composite seed distribution map.

12. The brachytherapy seed localizer of claim 11, wherein the composite seed distribution map is generated as a function of a distance metric between the tracked seed distribution map and the reconstructed seed distribution map.

13. The brachytherapy seed localization system of claim 12, wherein the estimated locations of the radioactive seeds within the ultrasound space of the diseased tissue include at least one of the delivered locations of the radioactive seeds within the ultrasound space of the diseased tissue and at least one of the projected locations of the radioactive seeds within the ultrasound space of the diseased tissue as a function of the distance metric between the tracked seed distribution map and the reconstructed seed distribution map.

14. The brachytherapy seed localizer of claim 12, wherein the estimated locations of the radioactive seeds within the ultrasound space of the diseased tissue exclusively include the delivered locations of the radioactive seeds within the ultrasound space of the diseased tissue as a function of the distance metric between the tracked seed distribution map and the reconstructed seed distribution map.

15. The brachytherapy seed localizer of claim 12, wherein the estimated locations of the radioactive seeds within the ultrasound space of the diseased tissue exclusively include the projected locations of the radioactive seeds within the ultrasound space of the diseased tissue excluding the at least one false projected location of the radioactive seed within the ultrasound space of the diseased tissue as a function of the distance metric between the tracked seed distribution map and the reconstructed seed distribution map.

* * * * *